US012599483B2

(12) United States Patent
Lee et al.

(10) Patent No.: US 12,599,483 B2
(45) Date of Patent: *Apr. 14, 2026

(54) SYSTEM AND METHOD FOR JOINING BONEY STRUCTURES

(71) Applicant: Randall F. Lee, Southlake, TX (US)

(72) Inventors: Randall F. Lee, Southlake, TX (US); Daniel S. Savage, Brecksville, OH (US); Alan W. Rorke, Bristol Avon (GB)

(73) Assignee: Randall F. Lee, Southlake, TX (US)

( * ) Notice: Subject to any disclaimer, the term of this patent is extended or adjusted under 35 U.S.C. 154(b) by 152 days.

This patent is subject to a terminal disclaimer.

(21) Appl. No.: 18/485,363

(22) Filed: Oct. 12, 2023

(65) Prior Publication Data

US 2024/0115389 A1 Apr. 11, 2024

Related U.S. Application Data

(60) Continuation of application No. 17/372,327, filed on Jul. 9, 2021, now Pat. No. 11,839,547, which is a (Continued)

(51) Int. Cl.
| | |
|---|---|
| *A61F 2/44* | (2006.01) |
| *A61B 17/80* | (2006.01) |
| *A61B 17/84* | (2006.01) |
| *A61F 2/30* | (2006.01) |
| *A61F 2/46* | (2006.01) |

(Continued)

(52) U.S. Cl.
CPC ...... *A61F 2/30749* (2013.01); *A61B 17/8004* (2013.01); *A61B 17/844* (2013.01); *A61F 2/4603* (2013.01); *A61B 2017/564* (2013.01);

*A61B 2017/681* (2013.01); *A61B 17/846* (2013.01); *A61F 2002/30622* (2013.01); *A61F 2/4202* (2013.01); *A61F 2/4455* (2013.01)

(58) Field of Classification Search
CPC .............. A61B 17/8004; A61B 17/844; A61F 2/30749; A61F 2/4603
See application file for complete search history.

(56) References Cited

U.S. PATENT DOCUMENTS

| | | | |
|---|---|---|---|
| 3,506,982 A | 4/1970 | Steffee | |
| 3,552,389 A | 1/1971 | Martin et al. | |

(Continued)

FOREIGN PATENT DOCUMENTS

| | | |
|---|---|---|
| AU | 2013224006 B | 2/2017 |
| CA | 2635537 C | 5/2014 |

(Continued)

OTHER PUBLICATIONS

International Search Report, by the ISA/US, mailed Jan. 24, 2022, regarding PCT/US2021/051348.

(Continued)

*Primary Examiner* — Sameh R Boles
(74) *Attorney, Agent, or Firm* — Law Office of Bill Naifeh

(57) ABSTRACT

Disclosed are system and methods that use at least one non-threaded anchor and an implant with at least one aperture to join boney structures, where the interaction of the head of the anchor with the implant aperture causes the anchor to move transversely with respect to an initial trajectory. This movement causes compression or distraction of the boney structures which are coupled to the anchors.

7 Claims, 9 Drawing Sheets

Related U.S. Application Data division of application No. 17/248,943, filed on Feb. 13, 2021, now Pat. No. 11,058,542.

(60) Provisional application No. 63/130,323, filed on Dec. 23, 2020, provisional application No. 63/113,886, filed on Nov. 15, 2020, provisional application No. 63/081,187, filed on Sep. 21, 2020.

(51) Int. Cl.

| | |
|---|---|
| *A61B 17/56* | (2006.01) |
| *A61B 17/68* | (2006.01) |
| *A61F 2/42* | (2006.01) |

(56) References Cited

U.S. PATENT DOCUMENTS

| | | |
|---|---|---|
| 4,484,570 A | 11/1984 | Sutter et al. |
| 4,790,303 A | 12/1988 | Steffee |
| 6,984,234 B2 | 1/2006 | Bray |
| 7,488,320 B2 | 2/2009 | Middleton |
| 7,572,280 B2 | 8/2009 | Dickinson et al. |
| 8,267,997 B2 | 9/2012 | Colleran |
| 8,268,000 B2 | 9/2012 | Waugh et al. |
| 8,328,872 B2 | 12/2012 | Duffield et al. |
| 8,361,155 B2 | 1/2013 | Lambrecht et al. |
| 8,540,769 B2 | 9/2013 | Janowski et al. |
| 8,641,766 B2 | 2/2014 | Donner et al. |
| 8,764,831 B2 | 7/2014 | Lechmann et al. |
| 8,882,775 B2 | 11/2014 | Laposta et al. |
| 8,968,405 B2 | 3/2015 | Kirwan et al. |
| 8,979,930 B2 | 3/2015 | Glazer |
| 9,351,847 B2 | 5/2016 | Reed et al. |
| 9,408,715 B2 | 8/2016 | Donner et al. |
| 9,526,620 B2 | 12/2016 | Slivka et al. |
| 9,566,165 B2 | 2/2017 | Lee et al. |
| 9,937,055 B1 | 4/2018 | Bernhardt et al. |
| 10,022,161 B2 | 7/2018 | Blain et al. |
| 10,098,755 B2 | 10/2018 | Kaufmann et al. |
| 10,195,051 B2 | 2/2019 | Bergey et al. |
| 10,245,156 B2 | 4/2019 | Chataigner et al. |
| 10,258,479 B2 | 4/2019 | Stewart et al. |
| 10,376,377 B2 | 8/2019 | Seifert et al. |
| 10,433,975 B2 | 10/2019 | Ashleigh et al. |
| 10,478,310 B2 | 11/2019 | Ameil et al. |
| 10,485,591 B2 | 11/2019 | Lequette et al. |
| 10,631,999 B2 | 4/2020 | Gilbride et al. |
| 10,758,370 B2 | 9/2020 | Gilbride et al. |
| 11,058,542 B1 | 7/2021 | Lee et al. |
| 11,160,589 B1 | 11/2021 | Lee et al. |
| 11,839,547 B2 | 12/2023 | Lee et al. |
| 11,872,141 B2 | 1/2024 | Lee et al. |
| 2005/0182408 A1 | 8/2005 | Pfefferle et al. |
| 2006/0195094 A1 | 8/2006 | K et al. |
| 2009/0210062 A1 | 8/2009 | Thalgott et al. |
| 2009/0254126 A1 | 10/2009 | Orbay et al. |
| 2011/0098747 A1 | 4/2011 | Donner et al. |
| 2012/0078371 A1 | 3/2012 | Gamache et al. |
| 2012/0078373 A1 | 3/2012 | Gamache et al. |
| 2013/0079879 A1 | 3/2013 | Suh |
| 2013/0150968 A1 | 6/2013 | Dinville et al. |
| 2013/0166029 A1 | 6/2013 | Dinville et al. |
| 2013/0245767 A1 | 9/2013 | Lee et al. |
| 2014/0180417 A1 | 6/2014 | Bergey |
| 2015/0127109 A1 | 5/2015 | Brett et al. |
| 2016/0074172 A1 | 3/2016 | Lee et al. |
| 2016/0106550 A1 | 4/2016 | Slivka et al. |
| 2016/0151171 A1 | 6/2016 | Mozeleski et al. |
| 2016/0338853 A1 | 11/2016 | Donner et al. |
| 2017/0007305 A1 | 1/2017 | Hollis et al. |
| 2017/0071750 A1 | 3/2017 | Urban et al. |
| 2017/0246007 A1 | 8/2017 | Chataigner et al. |
| 2018/0177606 A1 | 6/2018 | Reed et al. |
| 2018/0214280 A1 | 8/2018 | Seifert et al. |
| 2018/0325694 A1 | 11/2018 | Petersheim et al. |
| 2019/0000637 A1 | 1/2019 | Gilbride et al. |
| 2019/0000638 A1 | 1/2019 | Gilbride et al. |
| 2019/0105174 A1 | 4/2019 | Kaufmann et al. |
| 2019/0183658 A1 | 6/2019 | Lambrecht et al. |
| 2019/0328540 A1 | 10/2019 | Seifert et al. |
| 2022/0087820 A1 | 3/2022 | Lee et al. |
| 2022/0087821 A1 | 3/2022 | Lee et al. |
| 2023/0225775 A1 | 7/2023 | Lee et al. |
| 2023/0225869 A1 | 7/2023 | Lee et al. |

FOREIGN PATENT DOCUMENTS

| | | |
|---|---|---|
| CN | 108969163 A | 12/2018 |
| EP | 1968464 B1 | 2/2012 |
| EP | 2419030 B1 | 1/2017 |
| EP | 2701638 B1 | 5/2017 |
| EP | 3207900 B1 | 7/2018 |
| EP | 3470022 A1 | 4/2019 |
| FR | 2954692 A1 | 7/2011 |
| FR | 3005569 A1 | 11/2014 |
| FR | 3016793 A1 | 7/2015 |
| JP | 2017507000 A | 3/2017 |
| JP | 2018187417 A | 11/2018 |
| KR | 101555317 B | 10/2015 |
| KR | 101636010 B | 7/2016 |
| KR | 20160145538 A | 12/2016 |
| RU | 2631208 C2 | 9/2017 |
| WO | 2010121028 A2 | 10/2010 |
| WO | 2011129973 A1 | 10/2011 |
| WO | 2013062716 A1 | 5/2013 |
| WO | 2016100158 A1 | 6/2016 |
| WO | 2017029301 A1 | 2/2017 |
| WO | 2017087020 A1 | 5/2017 |
| WO | 2017186966 A1 | 11/2017 |
| WO | 2018140352 A1 | 8/2018 |
| WO | 2022061278 A1 | 3/2022 |
| WO | 2022061302 A1 | 3/2022 |

OTHER PUBLICATIONS

International Search Report, by the ISA/US, mailed Jan. 25, 2022, regarding PCT/US2021/051250.

Notice of Allowance, mail Jul. 1, 2021, by the USPTO, re U.S. Appl. No. 17/175,649.

Notice of Allowance, mailed Apr. 28, 2021, by the USPTO, re U.S. Appl. No. 17/248,943.

Notice of Allowance, mailed Sep. 13, 2023, by the USPTO, re U.S. Appl. No. 17/372,327.

Office Action, mailed Apr. 19, 2021, by the USPTO, regarding U.S. Appl. No. 17/175,649.

Office Action, mailed Jun. 2, 2023, by the USPTO, re U.S. Appl. No. 17/372,327.

Office Action-Restriction Requirement, mailed Apr. 6, 2021, by the USPTO, re U.S. Appl. No. 17/248,943.

Office Action-Restriction Requirement, mailed Mar. 30, 2021, by the USPTO, re U.S. Appl. No. 17/175,649.

Written Opinion, by the ISA/US, mailed Jan. 24, 2022, regarding PCT/US2021/051348.

Written Opinion, by the ISA/US, mailed Jan. 25, 2022, regarding PCT/US2021/051250.

Office Action, dated Mar. 5, 2025, by the USPTO, re U.S. Appl. No. 17/513,993.

Office Action, dated Oct. 20, 2025, by the USPTO, re U.S. Appl. No. 17/513,993.

Office Action, dated Oct. 28, 2025, by the USPTO, in U.S. Appl. No. 18/123,739.

Office Action-Restriction, dated Aug. 13, 2025, by the USPTO, re U.S. Appl. No. 18/123,739.

Office Action-Restriction, dated Sep. 8, 2025, by the USPTO, in U.S. Appl. No. 18/123,765.

Final Office Action, mailed Jun. 25, 2025, by the USPTO, in U.S. Appl. No. 17/513,993.

Notice of Allowance, mailed Feb. 2, 2026, by the USPTO, in U.S. Appl. No. 18/123,765.

(56)                    References Cited

OTHER PUBLICATIONS

Notice of Allowance, dated Mar. 5, 2026, by the USPTO, in U.S.
Appl. No. 18/123,739.

SYSTEM AND METHOD FOR JOINING BONEY STRUCTURES

CROSS REFERENCE TO RELATED APPLICATIONS

This application is a continuation of U.S. patent application Ser. No. 17/372,327, filed Jul. 9, 2021, which is a divisional of U.S. patent application Ser. No. 17/248,943, filed Feb. 13, 2021, now U.S. Pat. No. 11,058,542, and claims the benefit of the filing dates of the following U.S. provisional patent applications: U.S. Patent Application Ser. No. 63/081,187, filed on Sep. 21, 2020, entitled SYSTEM AND METHOD FOR JOINING BONEY STRUCTURES; U.S. Patent Application Ser. No. 63/113,886, filed on Nov. 15, 2020, entitled SYSTEM AND METHOD FOR JOINING BONEY STRUCTURES; U.S. Patent Application Ser. No. 63/130,323, filed on Dec. 23, 2020, entitled SYSTEM AND METHOD FOR JOINING BONEY STRUCTURES; the disclosures of all of the above patent applications are hereby incorporated by reference for all purposes. This application also incorporates by reference for all purposes a commonly owned patent application entitled SYSTEM AND METHOD FOR JOINING BONEY STRUCTURES, U.S. patent application Ser. No. 17/175,649, filed Feb. 13, 2021.

TECHNICAL FIELD

The disclosed invention relates in general to orthopedic and dental surgically implanted devices, and in particular to implantable devices which use a plurality of non-threaded anchors with an implant or plate to compress and join boney structures.

BACKGROUND INFORMATION

Over a hundred years ago surgeons determined that a combination of screws and plates worked as a method of internal fixation of two or more bone structures. In time surgeons empirically learned that placing two or more bones in mechanical compression greatly improved the speed and quality of bone healing. Mechanical compression was then rendered through external devices and internally fixated with the screw plate device.

Many believe that localized bone compression is the orthopaedic standard for bone healing. Current art uses plates with dedicated screw channels or directive apertures that determine the range of screw angulation and the resultant course of the screw's trajectory.

In many orthopedic related procedures, however, such as spinal, sternal chest closure, dental, and numerous orthopedic reconstructions, plates and screws have not been found to follow compressive bone healing principals. Instead, the screw plate configurations stabilize the boney structures, but do not typically compress the bone structures together. Furthermore, threaded anchors such as screws have many disadvantages, including the tendency to back out of a boney structure over time.

Therefore, what is needed is a novel plate anchor system that consistently achieves bone compression or distraction of two boney structures together.

SUMMARY

In response to these and other problems, in one embodiment, there is a system that includes non-threaded anchors that follow a trajectory into a boney structure and then a non-threaded head of the anchor interacts with the aperture features in an implant to cause the head of the anchor to move transversely which can cause compression or distraction of boney structures coupled to the anchors.

These and other features, and advantages, will be more clearly understood from the following detailed description taken in conjunction with the accompanying drawings. It is important to note the drawings are not intended to represent the only aspect of the invention.

BRIEF DESCRIPTION OF THE DRAWINGS

FIGS. 1E through 1H are transverse sectional views of the non-threaded anchor of FIG. 1A.

DETAILED DESCRIPTION

Figures 1A, 1B:
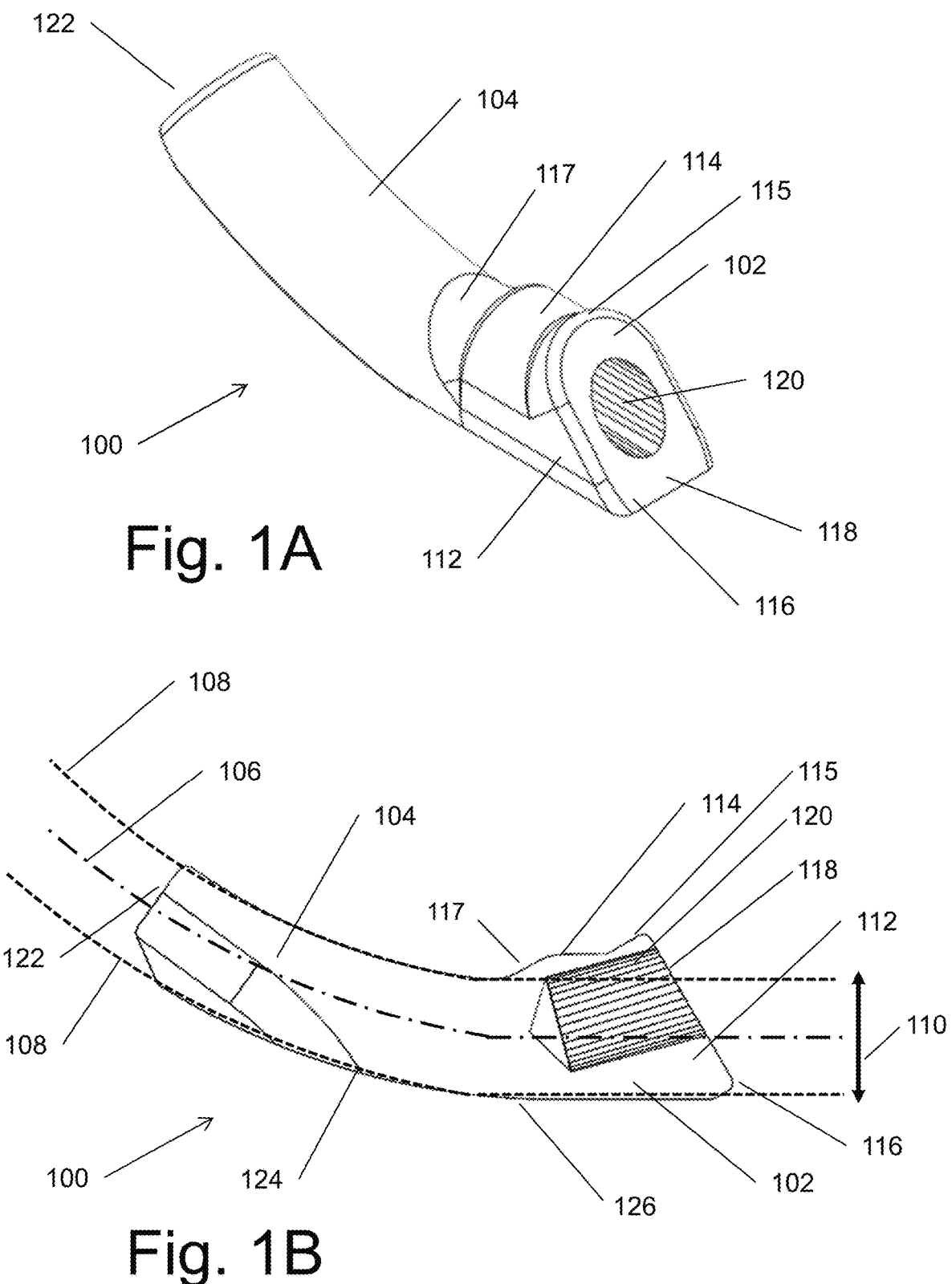
FIG. 1A is a perspective view of one aspect of a non-threaded anchor which can be used in one or more aspects of the present invention.
FIG. 1B is a longitudinal section view of the non-threaded anchor of FIG. 1A.

For the purposes of promoting an understanding of the principles of the present inventions, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

When directions, such as upper, lower, top, bottom, clockwise, counter-clockwise, are discussed in this disclosure, such directions are meant to only supply reference directions for the illustrated figures and for orientation of components in respect to each other or to illustrate the figures. The directions should not be read to imply actual directions used in any resulting invention or actual use. Under no circumstances, should such directions be read to limit or impart any meaning into the claims.

Figure 1C:
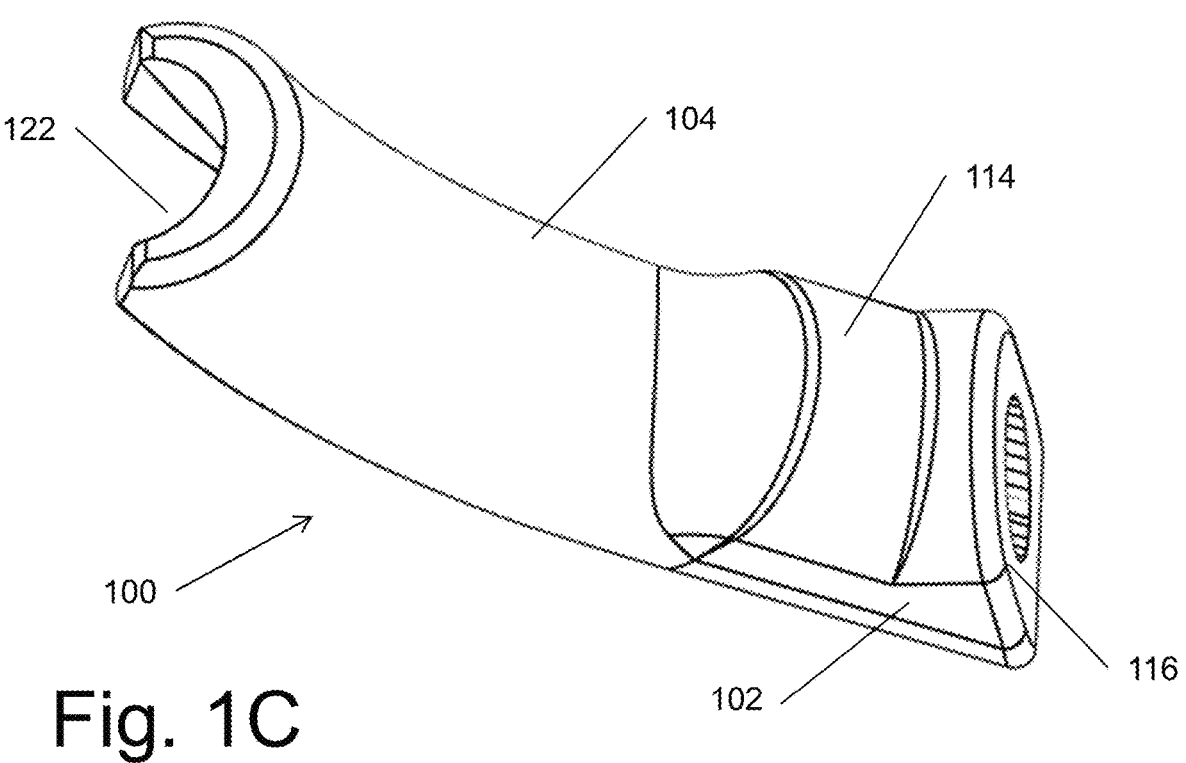
FIG. 1C is a top perspective view of the non-threaded anchor of FIG. 1A orientated so that the distal end is illustrated.
Figure 1D:
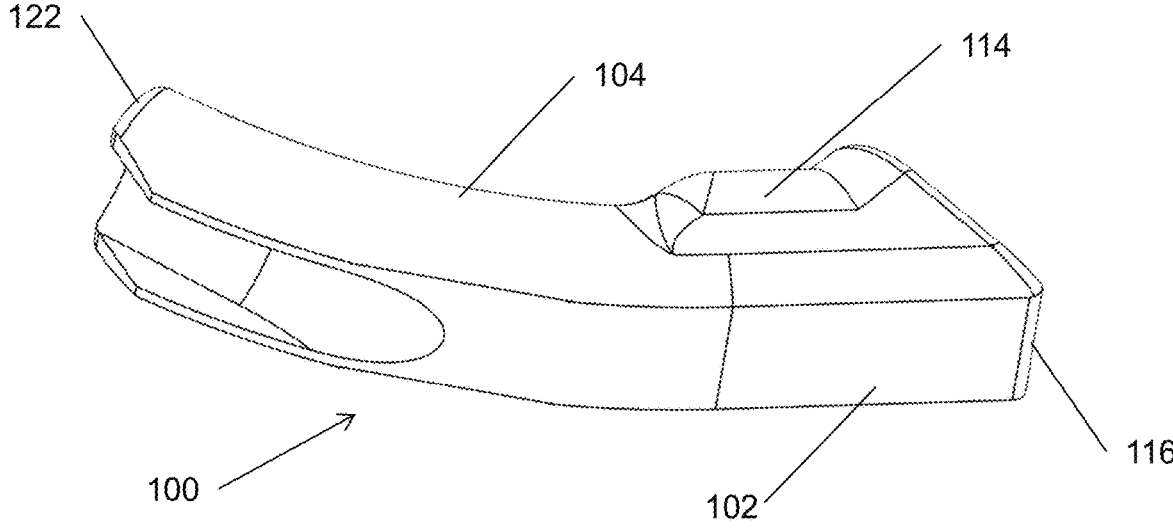
FIG. 1D is a bottom perspective view of the non-threaded anchor of FIG. 1A.

Anchors:

FIG. 1A is a proximal perspective view of one aspect of a non-threaded anchor 100 which can be used with several embodiments of the present invention. FIG. 1B is a longitudinal section view of the non-threaded anchor 100. FIG. 1C is a top perspective view of the anchor 100 orientated to illustrate a distal end 122. In contrast, FIG. 1D is a bottom perspective view of the anchor 100.

Turning now to FIGS. 1A through 1D, in the illustrative embodiment, the non-threaded anchor 100 includes a non-threaded proximal end or head portion 102 which is coupled to a non-threaded longitudinal body portion 104. The non-threaded elongated body 104 has a longitudinal or center axis 106, which in this embodiment, partially defines an initial trajectory into a boney structure as will further be discussed below. In the illustrated embodiment, the head portion 102 and the elongated body portion 104 share central axis 106 and the central axis 106 is curved within the elongated body portion 104 and straight within the head portion 102. In other embodiments, the elongated body portion 104 may be straight in which the center axis 106 would also be straight. In yet other embodiments, the head portion 102 may be curved and likewise, the center axis 106 within the head portion may also be curved.

FIG. 1B is a section view of the anchor 100 with the addition of dotted lines 108. For purposes of illustration, the dotted lines 108 are boundary lines that represent the portion of the anchor 100 that is generally equal distance with respect to the center axis 106 in a direction 110 that is generally normal or transverse to the direction of the center axis 106. For purposes of this disclosure, any portion of the head portion 102 that is outside of the dotted lines 108 is defined as "offset" or eccentric to the center axis 106. As can be seen most clearly in FIG. 1B, the non-threaded head portion 102 includes a first or symmetrical head portion 112 that is substantially within the boundary lines 108 and a second or offset portion 114 of the head portion 102 that is outside of the boundary lines 108. Looking from the perspective of FIG. 1B, the boundary lines 108 are generally symmetrical or equal distance from the center axis 106 in a direction 110 which is normal to the center axis. Thus, for purposes of this disclosure, the second or offset portion 114 of the head portion 102 that is outside of the boundary lines 108 is defined as an offset portion 114 from the center axis. In other words, an unsymmetrical mass or structure beyond an equal distance line from the center axis is considered to be an "offset" portion of a head for purposes of this disclosure. A transition or blended surface 117 allows for the smooth transition between the surface of the elongated body portion 104 and the offset anchor head portion 114.

In certain embodiments, a proximal end 116 contains an engagement surface 118 that is angled with respect to the normal direction 110 of center axis 106. In certain embodiments, the engagement surface 118 may have engagement features, such as aperture 120 for engaging with various embodiments of insertion instruments as will be explained below. In the illustrative embodiment, the longitudinal axis of the aperture 120 may be angled with respect to the center axis 106.

In the illustrative embodiment, a crest 115 of the offset portion 114 is formed at the distal end of the engagement surface 118 as illustrated in FIG. 1B. The height of the offset portion 114 decreases as one moves along the longitudinal direction from the proximal end 116 towards the distal direction as illustrated in FIG. 1A and FIG. 1B. In certain embodiments, the oversized geometry of the offset portion 114 causes a light press fit between the anchor head portion 114 and the aperture of an implant. Thus, in some embodiments, the offset portion 114 may be an oversized geometric volume which contacts a surface of the aperture. These are cylindrical surfaces which will largely be concentric in the final position, and in the offset portion 114 they may have an incrementally larger radius than the underside of the surface in the aperture resulting in being wedged together in the final position—which assists in preventing the anchor from "backing out" of the respective aperture. In yet other embodiments, other anti-back methods and techniques may also be employed, such as blocker plates, retaining rings, and locking screws.

As can be best seen in FIGS. 1C and 1D, a distal end 122 of the anchor 100 is designed to penetrate and be pushed through a boney structure. Consequently, at the distal end 122 the cross-sectional area of the body portion 104 is significantly reduced which also reduces the force necessary to push the distal end 122 through the boney structure (not shown). In the illustrative embodiment as best seen in FIG. 1C, the distal end 122 has a generally semi-circular or horseshoe shaped cross-sectional area. For instance, FIG. 1E is a partial perspective view where the body portion 104 has been cut close to the distal end 122. The cut in FIG. 1E is in a vertical direction and illustrates the horseshoe shape of cross-section of the body portion 104 when the section is cut close to the distal end 122. In contrast, FIG. 1F is a partial perspective view where the body portion 104 has been cut at a point between the distal end 122 and a midsection point 124 (see FIG. 1B). The cut in FIG. 1F is in a vertical direction and illustrates a substantial thickening of the horseshoe shape of cross-section of the body portion 104.

FIG. 1G is a partial perspective view where the body portion 104 has been cut at the midsection point 124 (see FIG. 1B). The cut in FIG. 1G is in a vertical direction and illustrates a cross-sectional shape of a solid elliptical segment. As illustrated, the body portion 104 has a vertical thickness or height of h1 at this cut point. In contrast, FIG. 1H is a partial perspective view where the head portion 102 has been cut around a point 126 (see FIG. 1B). As illustrated, the head portion 102 has a vertical thickness or height of h2 at this cut point. The height of the head portion increases until the crest 115 is reached as explained above. Note the difference in between the height h1 in FIG. 1G and the height h2 in FIG. 1H is created by the offset portion 114 of the head portion 102 as discussed above.

Although the anchor 100 as illustrated and discussed above use a tapering horseshoe cross-sectional shape for the body portion 104, any cross-sectional shape could be used and still be within the inventive aspects of the present invention. Such shapes include triangular, diamond, rectangular, circular or equilateral polygon cross-sectional shapes or a combination thereof. For instance, a triangular cross-sectional shape could be used on the body portion 104 while the head portion 102 may be largely circular in cross-sectional shape. If such shapes are used, generally the body portion will taper down from the head portion 102 to the distal end 122. In other words, the cross sectional areas of the body portion 104 will decrease as the distal end is approached.

In certain embodiments, the anchors discussed above may be fabricated from any number of biocompatible implantable materials, including but not limited to Titanium Alloys (Ti 6Al4V ELI, for example), commercially pure titanium, Chromium Cobalt (Cr—Co) and/or stainless steels. In yet other embodiments, the anchors may also be manufactured from polymer, including Carbon Fiber Reinforced Polymer ("CFRP") with a high carbon mass percentage. Furthermore in some embodiments, as explained below, the anchors may be formed using a shape memory alloy, such as Nitinol®.

A First Embodiment of an Implant

Figure 2A:
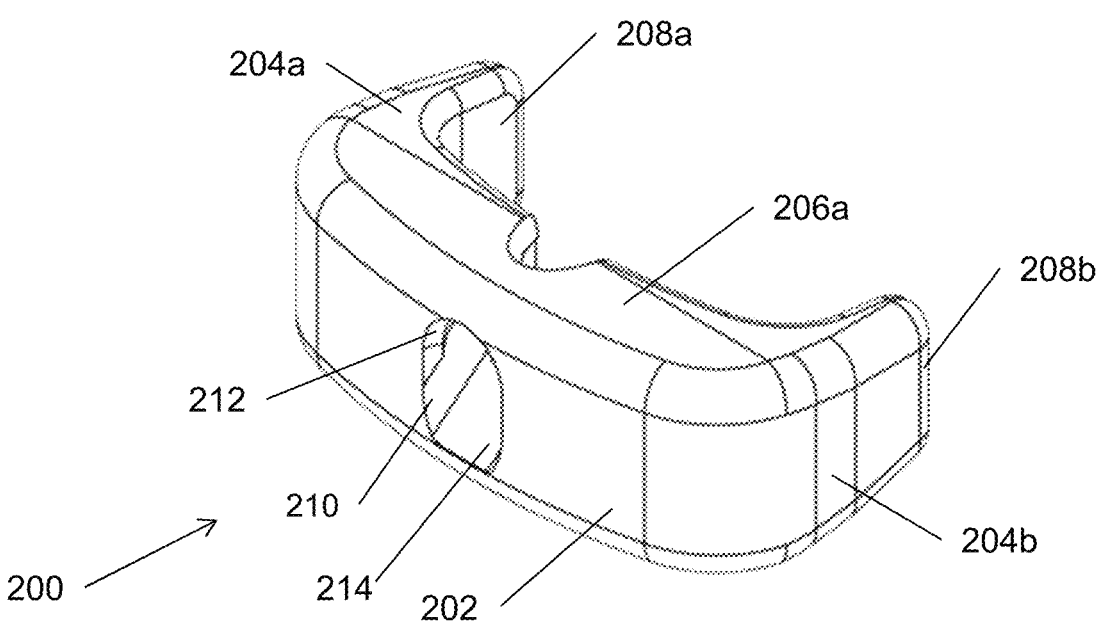
FIG. 2A is an isometric view of one embodiment of an implant which can be used with different aspects of the present invention.

Turning now to FIG. 2A, there is presented one embodiment of an interbody or interbone implant (also known in the art as an implant, insert plate, or insert). The interbody implant 200 can be used with the anchor 100 discussed above. The implants disclosed herein, such as implant 200, may be manufactured from any number of implant grade materials, including, but not limited to Titanium and Titanium Alloys, as well as Carbon Fiber Reinforced Polymer (CFRP).

In certain embodiments, the implant 200 may be generally C-shaped having a main body portion 202 with lateral side elements 204a and 204b opposing each other. There may be an upper bone engaging surface 206a and a lower bone engaging surface 206b (not shown). In certain embodiments, the implant 200 may form a structure to partially receive a cage or spacer (not shown). In certain embodiments, the lateral side elements 204a and 204b may gradually decrease or increase in height in an anterior to posterior direction with respect to a human body in order to generally conform the implant 200 to the geometry of the cage, spacer or boney body. In certain embodiments, the lateral side elements 204a and 204a may have engaging features (not shown in FIG. 2A) defined at their distal ends 208a and 208b configured to releasably engage retaining features of the cage or spacer. In other embodiments, the implant 200 may be designed to work as a stand-alone implant.

In certain embodiments, the main body portion 202 may have a central aperture 210 defined therethrough having an inner engagement surface 212. In certain embodiments, the aperture 210 may have a lower surface 214 defined therein sized to receive and engage a surface of the non-threaded anchor 100 discussed above. In certain embodiments, the interaction of the lower surface 214 with the longitudinal shape or geometry of the non-threaded anchor 100 defines an initial insertion trajectory for the non-threaded anchor. For purposes of this disclosure the "initial trajectory" is the path of movement of the elongated body portion 104 of an anchor 100 starting when the elongated body portion 104 is first introduced into the aperture 210 and ending when the head portion 102 of the anchor 100 first comes into contact with the engaging surfaces (such as engagement surface 212) forming a portion of the inside of the aperture 210.

A Method of Use

Figure 2B:
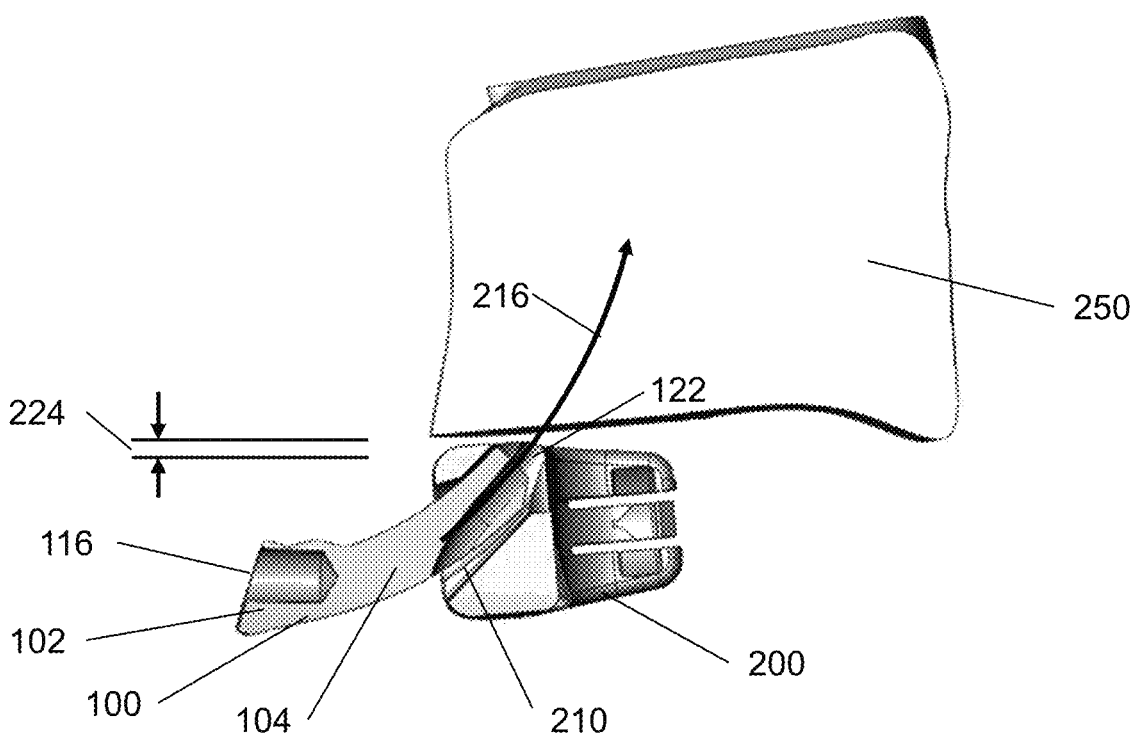
FIGS. 2B through 2F are sectional views illustrating the progression of one aspect of an anchor proceeding through the implant of FIG. 2A and a boney structure.

FIGS. 2B through 2F demonstrate a method of using one or more anchors 100 with the implant 200 to compress a boney structure 250 (such as a human vertebra) against implant 200. For purposes of this disclosure, a boney structure many be an entire human bone or a portion of a bone that has been fragmented or otherwise separated. FIGS. 2B through 2F are cross-sectional views of the implant 200, the boney structure 250, and the anchor 100 discussed above showing different stages of interaction between these elements. In FIG. 2B, the implant 200 is positioned adjacent to the boney structure 250. For purposes of explaining the illustrated embodiment, a gap 224 (not drawn to scale) is illustrated between the boney structure 250 and the implant 200. Additionally, for purposes of illustration, an initial trajectory of elongated body portion 104 of anchor 100 can be visualized as an arrow 216.

In FIG. 2B, the distal end 122 of the body portion 104 is illustrated as having been introduced into aperture 210. In certain embodiments, a non-torsional force may be applied onto the proximal end 116 of the head portion 102 to drive the first elongated body portion 104 through the central aperture 210 and into the boney structure 250 along the trajectory illustrated as arrow 216. In certain embodiments this non-torsional force may be a "smooth" non-torsional force as opposed to a series of impact forces. In yet other embodiments, an impact force or a rotating force may be applied to drive the elongated body portion 104 into the boney structure 250.

Figure 2C:
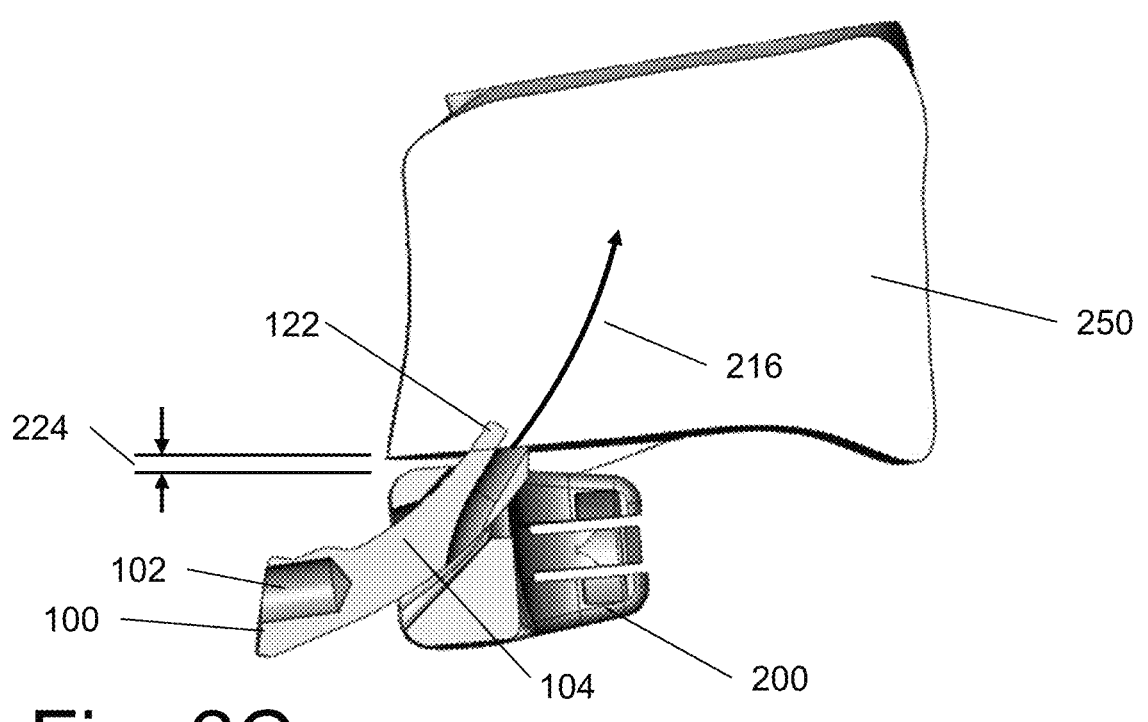
Figure 2D:
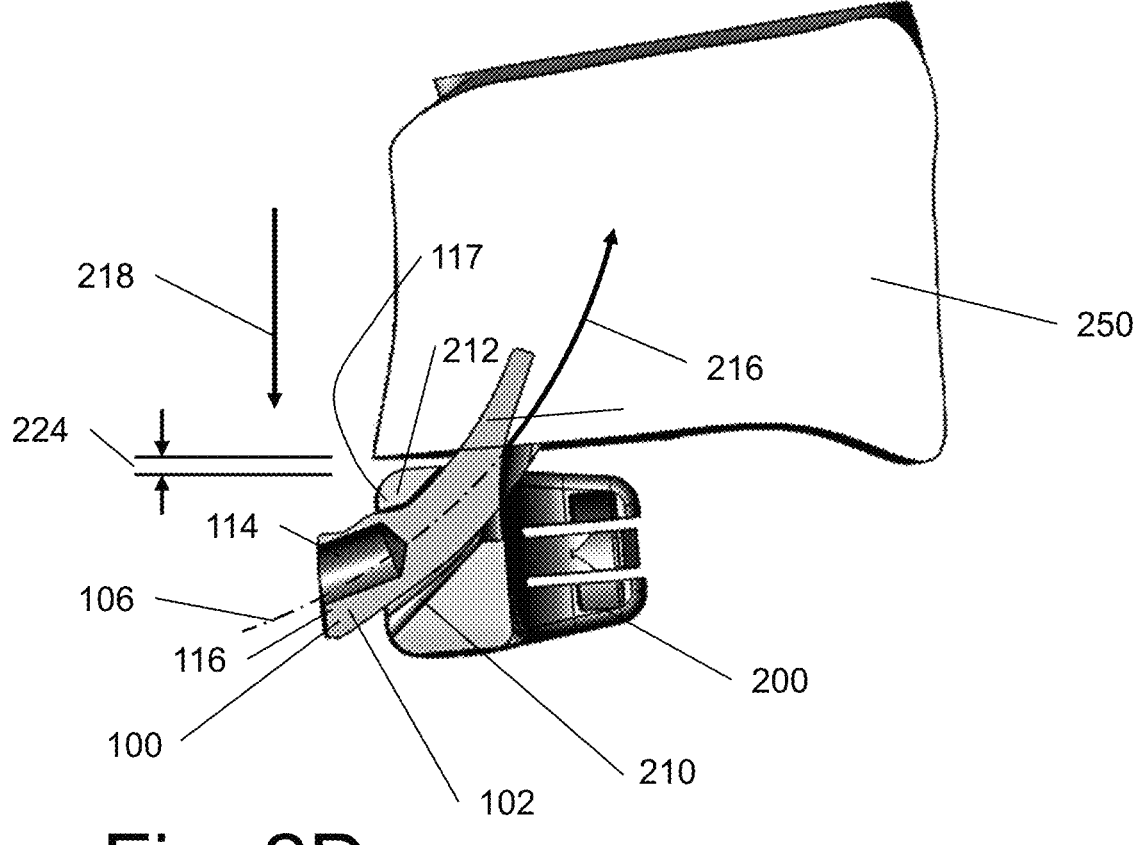

FIG. 2C illustrates the system and boney structure of FIG. 2B, but with the distal end 122 of elongated body portion 104 partially driven into the boney structure 250. Similarly, FIG. 2D illustrates the system and boney structure 250 of FIG. 2B, but with the elongated body portion 104 driven further into the boney structure 250. As can be seen in FIG. 2D, the elongated body portion 104 has now been mostly driven through the aperture 210 and is still following its initial trajectory as illustrated by arrow 216.

FIG. 2D also illustrates the situation where the non-torsional force continues to be applied onto the proximal end 116 of the head portion 102 as the transition surface 117 of head portion 102 begins to interact with the bone engaging surface 212 of the aperture 210. The interaction between the aperture 210 and the offset portion 114 of the head portion 102 (see above) forces the head in a direction that is generally transverse to the center axis 106 of the anchor 100. The direction of this transverse movement is represented by the arrow 218. The transition surface 117 allows for a smooth transition and kinematic transverse movement. The transverse movement of the head portion 102 also causes movement of the elongated body portion 104. Because the boney structure 250 is now attached to the body portion 104 as indicated in FIG. 2D, the first boney structure 250 is also forced to move in the transverse direction represented by arrow 218. Thus, causing the boney structure 250 to move closer to the implant 200.

Figure 2E:
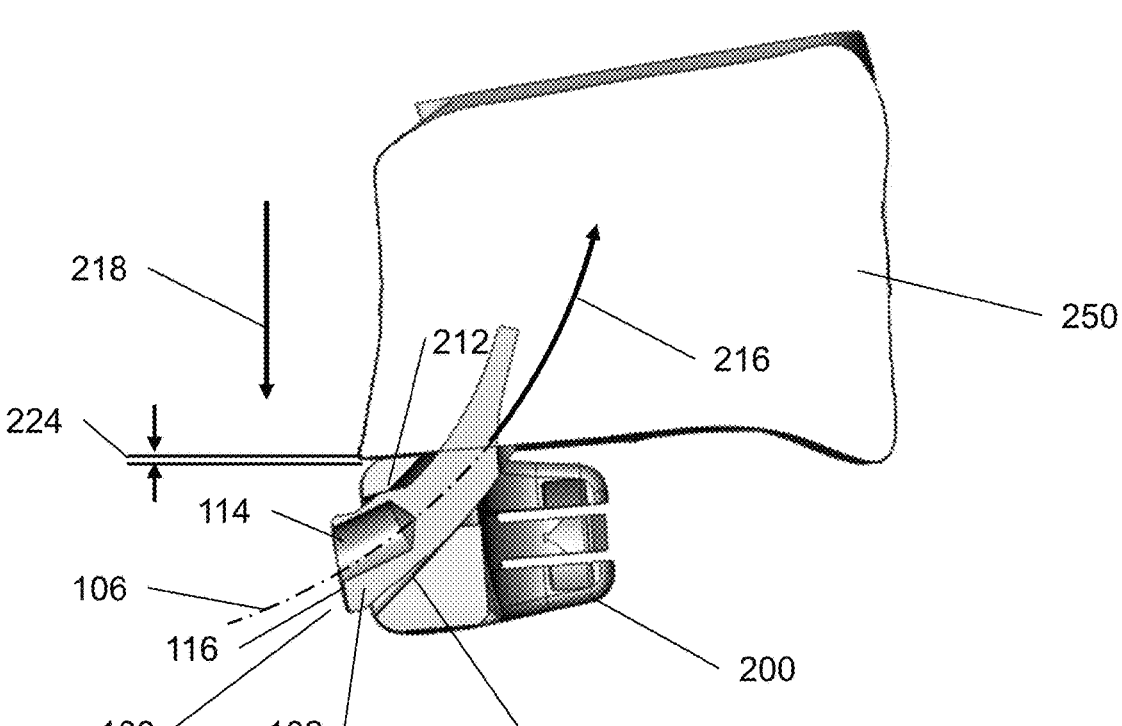

FIG. 2E illustrates the situation where the non-torsional force continues to be applied onto the proximal end 116 of the head portion 102 as the head portion is pushed further into the first aperture 210. The interaction between the inwardly sloped surface 212 of the aperture 210 and the offset portion 114 of the head portion 102 forces the head portion to keep moving in the transverse direction as represented by the arrow 218. As discussed above, the transverse movement of the head portion 102 also causes transverse movement of the elongated body portion 104, which causes the boney structure 250 to also move in the direction of arrow 218. Thus, causing the gap 224 to significantly narrow.

Figure 2F:
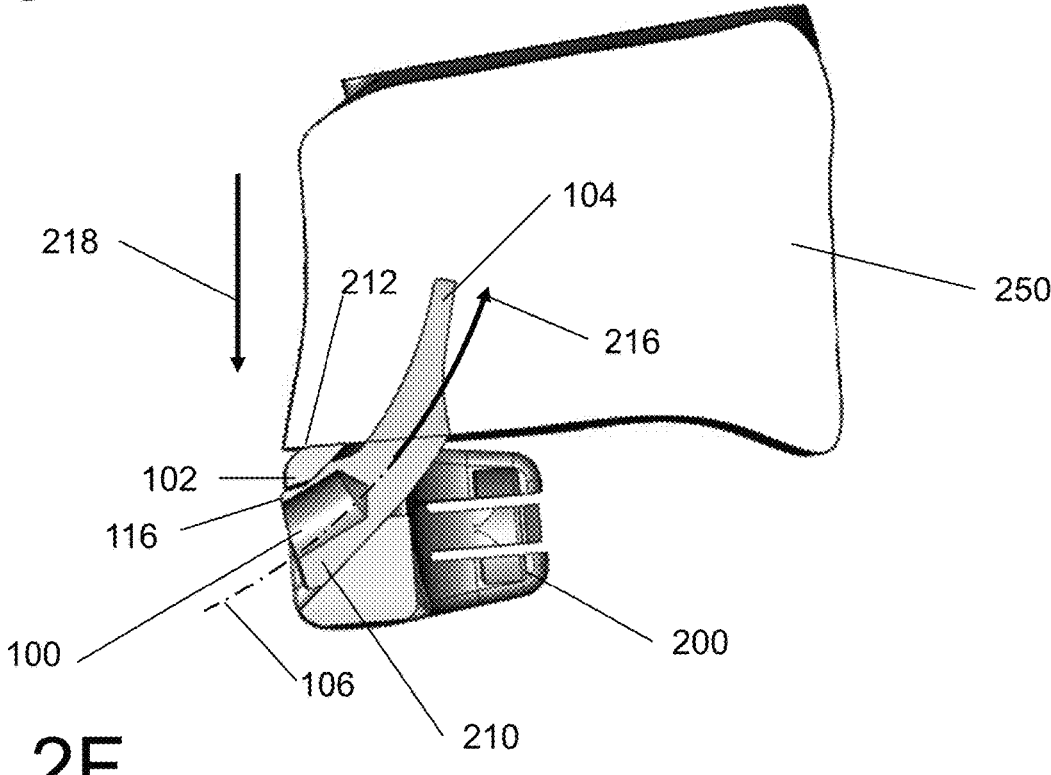

FIG. 2F illustrates the situation where the head portion 102 has been pushed completely into the aperture 210. As explained above, the interaction between the inwardly sloped surface 212 of the aperture 210 and the offset portion 112 of the head portion 102 has forced the head portion to move transversely in the direction of the arrow 218. The transverse movement of the head portion 102 also causes transverse movement of the elongated body portion 104, which causes the boney structure 250 to compress against the implant 200. The magnitude or height of the offset of the anchor head 102 determines the amount of compression achieved.

Multi-Anchor Embodiments

For purposes of simplification, the implant embodiments discussed above have illustrated and described with an implant and single anchor. However, the present invention contemplates the use of implant embodiment systems using two or more anchors. The use of two or more anchors will compress two adjacent boney structures together as explained below.

Figures 3A, 3B:
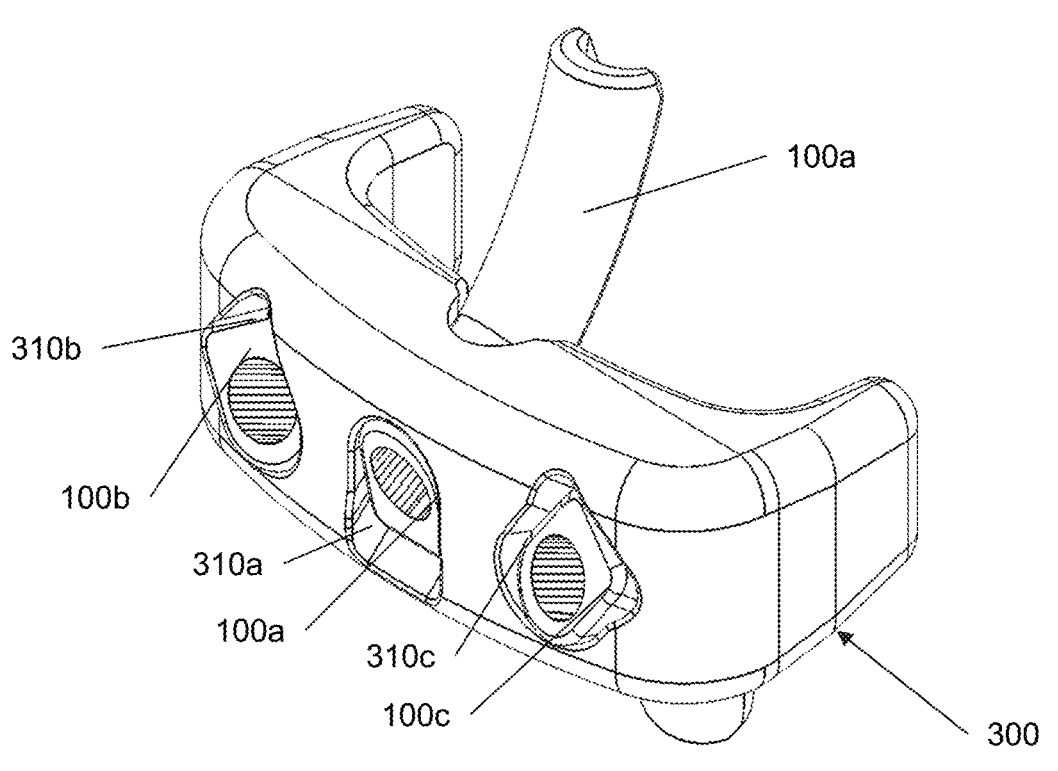
FIG. 3A is an isometric view of alternative embodiment of an implant which can be used with different aspects of the present invention.
FIG. 3B is a front view of the implant of FIG. 3A.

FIG. 3A is an isometric view of an implant 300 and three anchors, such as anchor 100 discussed above. FIG. 3B is a front or side view of the implant 300 with the three anchors. In the illustrative embodiment, implant 300 is similar to implant 200 discussed above except that implant 300 can accommodate three anchors: 100a, 100b, and 100c. Anchors 100a, 100b, and 100c are similar to anchor 100 discussed above with the subscribe reference letters added to distinguish the anchors from one another. For brevity and clarity, a description of those parts which are identical or similar to those described in connection with the first embodiment of the implant 200 or the anchor 100 will not be repeated here. Reference should be made to the foregoing paragraphs with the following description to arrive at a complete understanding of this embodiment.

Implant 300 defines a central aperture 310a which is curved in a generally upwards manner relative to the orientation of FIGS. 3A and 3B. Additionally, the implant 300 defines two side apertures 310b and 310c which in the illustrative embodiment are curved in a generally downward direction relative to orientation of FIGS. 3A and 3B (or in a direction that is flipped about a horizontal when compared to the central aperture 310a as illustrated in the figures). In certain embodiments, the side apertures 310b and 310c also are inclined relative to a vertical axis 301 and in some embodiments, the longitudinal axes of the apertures 310b and 310c converge at some point.

The anchor 100a is illustrated in FIGS. 3A and 3B as being fully inserted into the aperture 310a. Consequently, the anchor 100a is shown angled in an upwards position relative to FIGS. 3A and 3B. The anchors 100b and 100c are shown as being fully inserted into the apertures 310b and 310c, respectively. They are illustrated angled in a downwards position relative to the FIGS. 3A and 3B and their longitudinal axis are inclined and converge along the vertical axis 301.

Figure 3C:
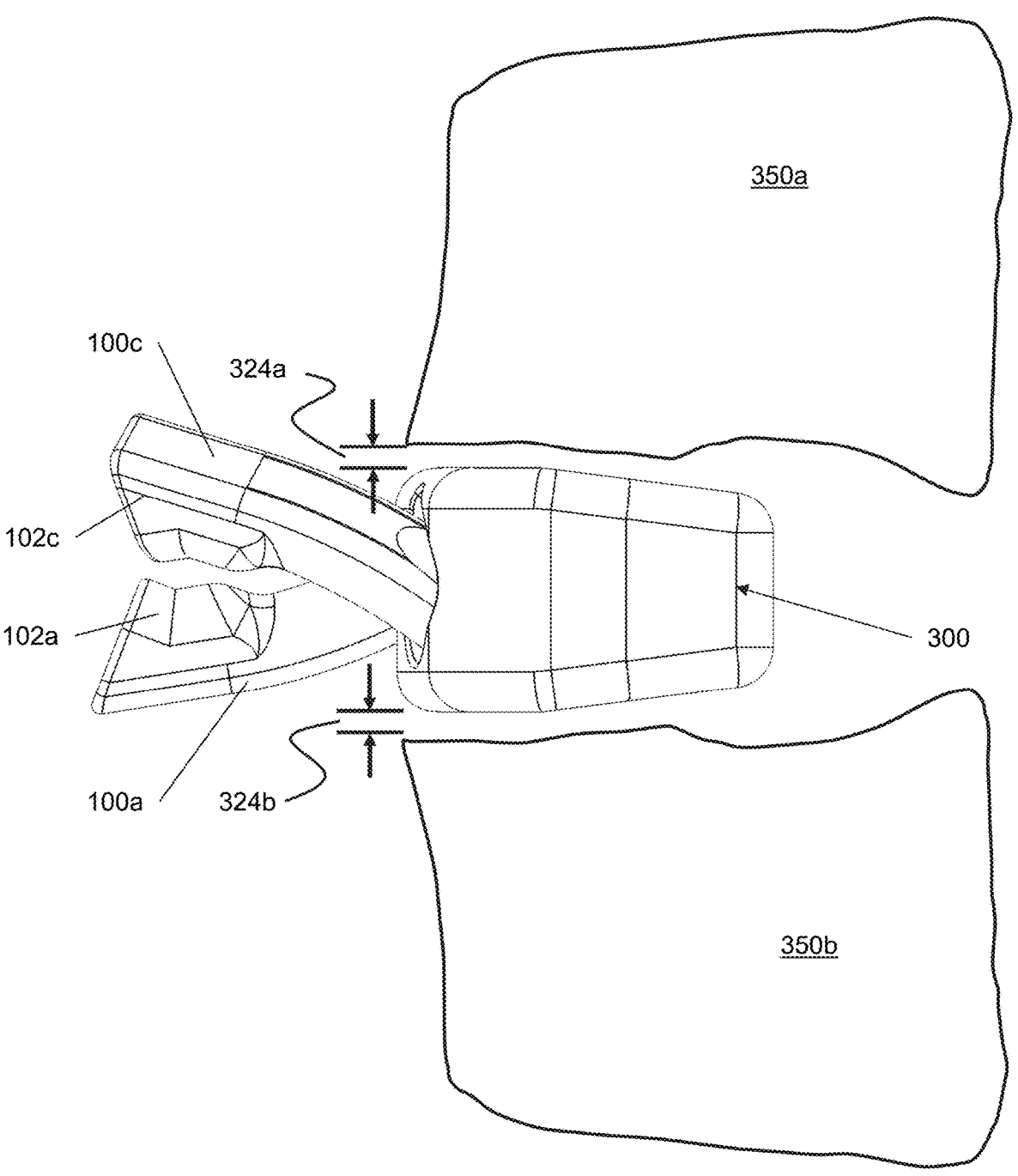
FIG. 3C is a side/sectional view of the implant of FIG. 3A with anchors in an un-deployed position.

In FIG. 3C, the implant 300 is illustrated sandwiched between two boney structures 350a and 350b (such as vertebrae of a human spine). The distal ends (not shown) of the anchors 100a, 100b, and 100c (anchor 100b is not visible in FIG. 3C because it is obscured by anchor 100c) are positioned within the implant 300 in a position similar to that shown with respect to the implant 200 in FIG. 2B above. For purposes of explaining the illustrated embodiment, a gap 324a (not drawn to scale) is shown between the boney structure 350a and the implant 300. Similarly, a gap 324b (not drawn to scale) is shown on the opposing side of the implant 300 between the boney structure 350b and the implant.

A method of compressing boney structure 350a to boney structure 350b via the implant 300 is similar to the method discussed above in reference to FIGS. 2B through 2F except that where the previous method joined the single boney structure 250 to an implant using a single anchor 100, this method joins two boney structures 350a and 350b to the implant 300 using two or more anchors. For instance, when a force is applied to the head 102a of the anchor 100a, the anchor will progress as described above in reference to FIGS. 2B through 2F to close the gap 324a and to compress the boney structure 350a against the implant 300. Simultaneously, or near simultaneously, additional forces are applied to the heads 102b (not shown in FIG. 3C) and 102c of the anchors 100b and 100c, respectively. Such forces will cause the anchors 100b and 100c to penetrate the boney structure 350b in a manner similar to the method described above in reference to FIGS. 2B through 2F. This penetration will close the gap 324b and cause the boney structure 350b to press against the implant 300 as explained above in reference to FIGS. 2B and 2F.

Figure 3D:
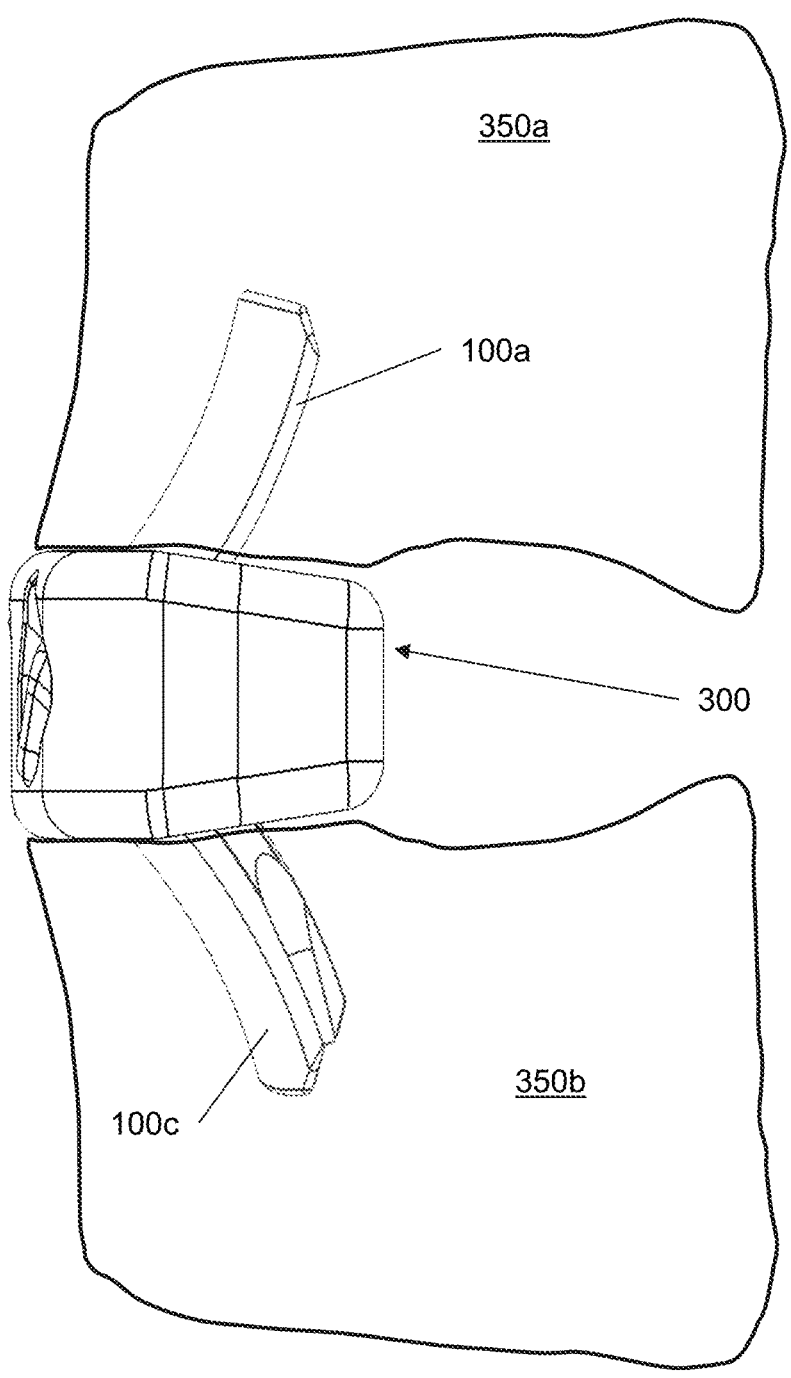
FIG. 3D is a side/sectional view of the implant of FIG. 3A with anchors in a fully deployed position.

In contrast, FIG. 3D shows the final positioning of the implant 300 with the anchors 100a, 100b, and 100c fully inserted into the implant 300 and the boney structures 350a and 350b in compression against the implant 300.

In alternative embodiments, one or more anchors may be a traditional anchor without an offset head portion. For instance in FIGS. 3A through 3D, the anchor 100a may be replaced with a traditional anchor (either threaded or non-threaded) having a symmetrical head portion. Similarly, the aperture 310a may be replaced with a traditional concentric aperture designed to accommodate an anchor with a concentric or symmetrical head. In this alternative embodiment, the symmetrical head and concentric aperture would not cause a transverse shift as explained above. Consequently, significant compression would not occur on the "upper" side of the implant. For example in FIG. 3C, if the anchor 100a is replaced with a traditional anchor and the aperture 310a is replaced with a symmetrical aperture, then only the boney structure 350b will significantly compress against the implant 300. The boney structure 350a only compresses against the implant 300 in as much as a traditional anchor would allow with any transverse shifting.

Although the above discussion focuses on compressing boney structures together or compressing a boney structure against an implant, the above anchors and methods could also be used to cause distraction between a first boney structure and a second boney structure via a modification of the anchors and implants. By reversing or flipping the head geometry (i.e. offset portions 114) of the anchors 100a, 100b, or 100c and reversing or flipping the engagement surfaces and geometries of the respective apertures 310a, 310b, and 310c of the implants 300, distraction of boney structures can be achieved by using the methods described above.

While the above example uses anchors 100 with the three aperture implant 300, implants may have one, two, three, four or more apertures and the corresponding number of anchors and still be within the scope of this invention.

Figure 4:
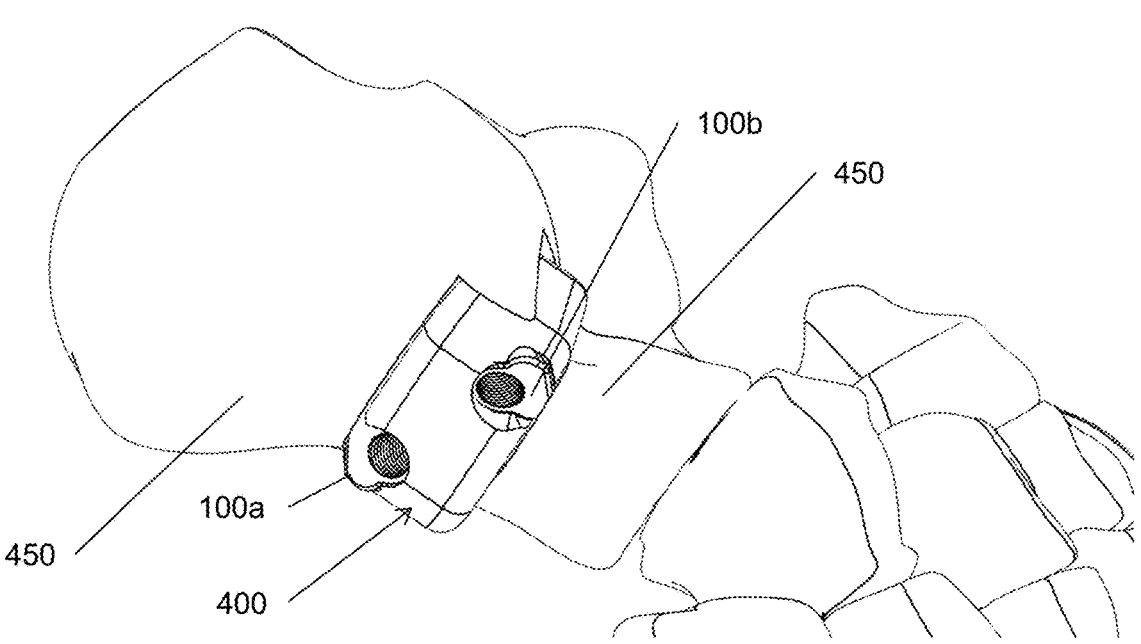
FIG. 4 is a two anchor embodiment used as an osteotomy wedge.
Figure 5:
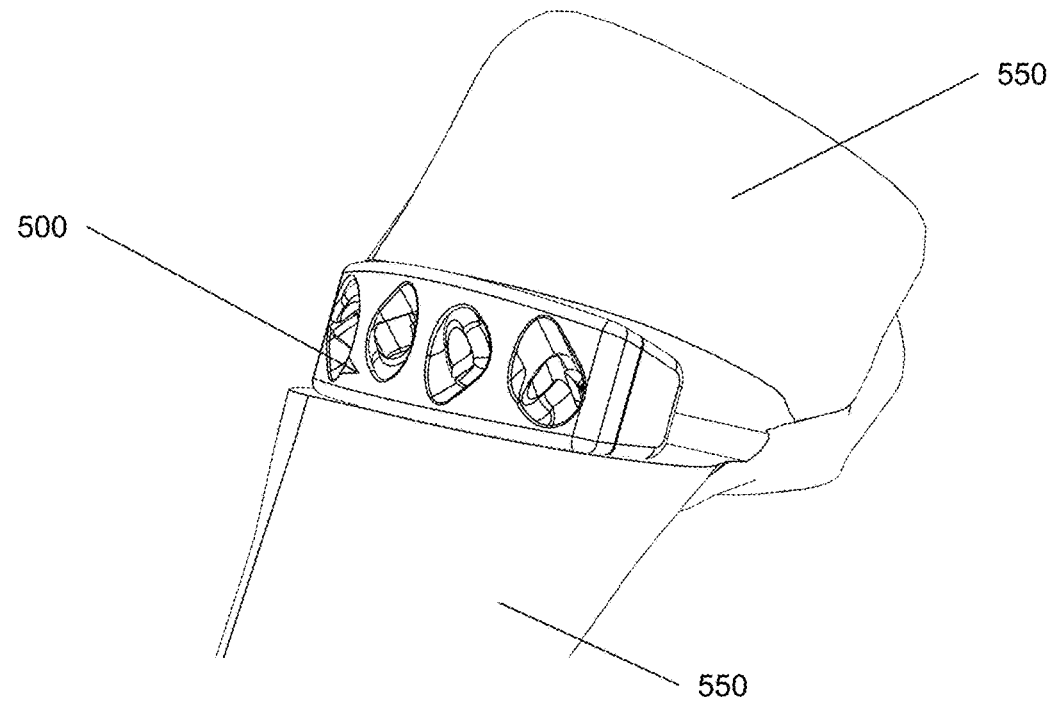
FIG. 5 is a four anchor embodiment used as an osteotomy wedge.

For instance, FIG. 4 depicts a perspective view of two anchor implant 400 joining a fractured re-aligned calcaneus 450 together (the Talus has been removed for clarity). The implant 400 and the associated two anchors 100a and 100b fixes and holds the osteotomies together. Other applications are possible. As an example, FIG. 5 is a perspective view of a top of a tibia 550 showing a four anchor implant 500 joining the top of the tibia together.

In yet other embodiments, various components, for example anchor 100 may be made from nickel titanium (also known as Nitinole) or another shape memory alloy. The anchor would have a very specific shape at a cooler temperature, such as room temperature. Once inserted into a human body, the metal would rise to a body temperature which will cause the anchor to change shape to enhance compression.

For instance, at or below room temperature a straight anchor might be inserted. At body temperature, the straight anchor turns into a curved anchor and applies additional compression or distraction. Similarly, a curved anchor could turn into a straight anchor at body temperature to enhance either compression or distraction.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

Any advantages and benefits described may not apply to all embodiments of the invention. When the word "means" is recited in a claim element, Applicant intends for the claim element to fall under 35 USC 112(f). Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word "means" are not intended to fall under 35 USC 112(f).

The foregoing description of the embodiments of the invention has been presented for the purposes of illustration and description. It is not intended to be exhaustive or to limit the invention to the precise form disclosed. Many combinations, modifications and variations are possible in light of the above teaching. For instance, in certain embodiments, each of the above described components and features may be individually or sequentially combined with other components or features and still be within the scope of the present invention. Undescribed embodiments which have interchanged components are still within the scope of the present invention. It is intended that the scope of the invention be limited not by this detailed description, but rather by the claims.

What is claimed is:

1. An implant system for joining boney structures comprising:
a first non-threaded anchor including,
a first non-threaded elongated body having a center axis,
a first non-threaded head coupled to a distal end of the elongated body, the first head including a first portion of the first head that is substantially concentric to the center axis and a second portion of the first head that is offset from the center axis;
a second non-threaded anchor including,
a second non-threaded elongated body having a center axis,
a second non-threaded head coupled to a distal end of the elongated body, the second head including a second portion of the second head that is substantially concentric to the center axis and a second portion of the second head that is offset from the center axis;
an implant including,
a first bone engaging surface and a second bone engaging surface;
a first aperture defined within the implant, the first aperture having a first proximal portion and a first distal portion exiting through the first bone engaging surface,
the first distal portion sized and to allow passage of the first elongated body along a first trajectory,

the first proximal portion sized and shaped to accept the first head only upon an occurrence of transverse movement of the first head with respect to the first trajectory;
a second aperture defined within the implant, the second aperture having a second proximal portion and a second distal portion exiting through the second bone engaging surface,
the second distal portion sized and to allow passage of the second elongated body along a second trajectory, and
the second proximal portion sized and shaped to accept the second head only upon an occurrence of transverse movement of the second head with respect to the second trajectory.

2. The system of claim 1, further comprising:
a third non-threaded anchor including,
a third non-threaded elongated body having a center axis,
a third non-threaded head coupled to a distal end of the elongated body, the third head including a third portion of the third head that is substantially concentric to the center axis and a third portion of the third head that is offset from the center axis;
wherein the implant also includes,
a third aperture defined within the implant, the third aperture having a third distal portion and a third proximal portion,
the third distal portion sized and to allow passage of the third elongated body along a third trajectory, and
the third proximal portion sized and shaped to accept the third head only upon an occurrence of transverse movement of the third head with respect to the third trajectory.

3. The system of claim 1, wherein the first aperture includes a first force applying surface sized and shaped to assert a transverse force on the second portion of the first head as the second portion of the first head slidingly engages the first force applying surface.

4. The system of claim 1, wherein the first aperture is curved in a first direction with respect to a center axis of the implant and the second aperture is curved in a second direction with respect to the center axis of the implant.

5. The system of claim 1, wherein the aperture includes a force applying surface sized and shaped to assert a transverse force on the second portion of the head as the second portion of the head slidingly engages the force applying surface.

6. The system of claim 1, wherein the aperture is curved in a first direction with respect to a center axis of the implant.

7. An implant system for joining boney structures comprising:
a non-threaded anchor including,
a non-threaded elongated body having a center axis,
a non-threaded head coupled to a distal end of the elongated body, the head including a first portion of the head that is substantially concentric to the center axis and a second portion of the head that is offset from the center axis;
an interbody implant including,
a first bone engaging surface and a second bone engaging surface;
an aperture defined within the implant, the aperture having
a proximal portion and a distal portion exiting through the first bone engaging surface, the distal portion sized and to allow passage of the elongated body along a trajectory, the proximal portion sized and shaped to accept the head only upon an occurrence of transverse movement of the head with respect to the trajectory.

\* \* \* \* \*